US00PP21081P2

(12) United States Plant Patent
Stemkens

(10) Patent No.: US PP21,081 P2
(45) Date of Patent: Jun. 22, 2010

(54) ***VERBENA* PLANT NAMED 'SCY'**
(50) Latin Name: *Verbena×hybrida*
Varietal Denomination: SCY

(75) Inventor: Henricus G. W. Stemkens, Andijk (NL)
(73) Assignee: Syngenta Crop Protection AG, Basel (CH)

( * ) Notice: Subject to any disclaimer, the term of this patent is extended or adjusted under 35 U.S.C. 154(b) by 0 days.
(21) Appl. No.: 12/322,207
(22) Filed: Jan. 29, 2009
(51) Int. Cl.
*A01H 5/00* (2006.01)
(52) U.S. Cl. ..... Plt./308
(58) Field of Classification Search ..... Plt./308
See application file for complete search history.

*Primary Examiner*—Kent L Bell
(74) *Attorney, Agent, or Firm*—S. Matthew Edwards

(57) ABSTRACT

A new *Verbena* plant named 'SCY' characterized particularly as to novelty by scarlet flowers with a striking white eye, which appear earlier on the plant, and a growing habit that is upright.

1 Drawing Sheet

Latin name of the genus and species of the plant claimed: *Verbena×hybrida.*

Varietal denomination: 'SCY'.

BACKGROUND OF THE NEW PLANT

The present invention comprises a new distinct cultivar of *Verbena*, botanically known as *Verbena×hybrida.*

The new *Verbena×hybrida* is a product of a planned breeding program conducted in Enkhuizen, Netherlands.

A new *Verbena* plant particularly distinguished by its scarlet flower with a clear white eye, early flowering, a spreading habit that is first semi-erect and later spreading.

The new cultivar is propagated from cuttings resulting from the cross-pollination of 'C0811-2' and 'D1473-2'. 'C0811-2' is a scarlet flowering *Verbena* having a spreading habit. 'C0811-2' is not commercially available and is not known by any synonyms. 'D1473-2' is a red- flowering plant having an erect habit. 'D1473-2' is not commercially available and is not known by any synonyms. Both 'C0811-2' and 'D1473-2' have not been patented.

As a result of this cross-pollination the present cultivar was created in 2003 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new *Verbena* plant is an annual in most climatical zones in the US, only in zones 8, 9 and 10 it is a perennial plant.

DESCRIPTION OF THE DRAWING

This new *Verbena* plant is illustrated by the accompanying photographic drawing which shows blooms, buds and foliage of the plant in full colour, the colour shown being as true as can be reasonably obtained by conventional photographic procedures.

DESCRIPTION OF THE NEW CULTIVAR

The following detailed descriptions set forth the distinctive characteristics of this new *Verbena*. The data which defines these characteristics were collected from asexual reproductions carried out in Enkhuizen, Netherlands. The plant history was taken on 14 week old plants, blossomed under natural light in a greenhouse.

Color readings were taken in the greenhouse under ambient light. Color references are primarily to the R.H.S. Colour Chart of The Royal Horticultural Society of London.

TABLE 1

Specification of differences with parents and most resembling variety

| Character | 'SCY' | 'C0811-2' | 'D1473-2' | Temari red with eye |
|---|---|---|---|---|
| Flower color | Scarlet with eye | Scarlet | Red | Red with eye |
| Earliness | Early | Early | Late | Late |
| Leaf size | Medium | Big | Small | Big |
| Plant size | Compact | Compact | Big | Big |

The plant:

*Classification.*—Botanical: *Verbena×hybrida.*

*Parentage.*—Female parent: 'C0811-2'. Pollen parent: 'D1473-2'.

*Growth habit.*—Semi-upright.

*Plant height.*—14–22 cm.

*Spreading area of plant.*—35–60 cm.

*Growth rate.*—Hanging and vigorous.

*Branching character.*—Freely branching and lateral branching at every node.

*Blooming period.*—From April until November.

The stem:

*Diameter.*—2.5–3 mm.

*Shape.*—Tetragonal.

*Anthocyan pigmentation.*—Absent.

*Color.*—137B.

*Length of internode.*—20–34 mm, depending on the light where the plant is propagated.

*Length of the total stem.*—26.5 cm.

*Pubescence.*—Pubescence is present.

The foliage:

*Phyllotaxis.*—Opposite.

*Shape of blade.*—Broadly ovate.

*Texture.*—Upper side: Pubescent. Lower side: Pubescent.

*Venation.*—Pinnate.

*Leaf margin.*—Simple incised.

*Leaf base.*—Shortly attenuate.
*Leaf apex.*—Acute.
*Length.*—25–34 mm.
*Width.*—18–28 mm.
*Depth of incision.*—2–3 mm.
*Colour.*—Upper side: 137A. Lower side: 137C.
*Pubescence.*—Some pubescence is present.
*Length of leaf stem.*—5–9 mm.
*Petiole surface structure.*—Slightly pubescent.
*Petiole color.*—Upper side: 137A.
*Petiole color.*—Lower side: 137C.
*Petiole diameter.*—3mm.

The bud:
*Peduncle length.*—30–50 mm, depending on season.
*Size.*—Diameter: 2 mm. Length: 6–10 mm.
*Shape.*—Elongated and ovate.
*Colour.*—137A.
*Sepals.*—Color both sides: 137A. Form: Upright. Number: 5, fused. Length: 5 mm. Width: 2 mm. Shape: Elongated. Apex: Acute. Base: Attenuate.

The flower:
*Facing direction.*—Upward.
*Outward curvature of petal.*—Slightly curved.
*Diameter.*—20 mm.
*Height.*—18–20 mm.
*Borne.*—In a cluster.
*Form.*—Salverform; sessile on terminal spikes.
*Cluster.*—Terminal spike.
*Color.*—Upper surface: 46B. Lower surface: 46C.
*Eye.*—A big (3 mm) Whitish Eye (155C) is present. All five petals exhibit this whitish coloration.
*Overlapping of petals.*—Separate.
*Number of petals.*—Gamopetalous, 5 lobed.
*Shape of the petals.*—Each petal is heart shaped at the apex and grown together at the base.
*Petal margin.*—Entire.
*Petal surface texture.*—Smooth.
*Size of the petal.*—Length: 6–9 mm. Width: 6–8 mm.
*Spike.*—Height: 25–32 mm. Diameter: 32–45 mm.
*Calyx length.*—8–10 mm.
*Anthocyan pigmentation of calyx limb.*—Absent.
*Color of the calyx.*—137A.
*Number of flowers per spike.*—20–35.
*Fragrance.*—No.
*Lastingness of the bloom.*—New florets continue to open in one spike over a period of 16 days.
*Lastingness of one flower.*—4 days on the plant and 3 hours off the plant.

Reproductive organs:
Androecium:
*Stamens quantity.*—4.
*Anther shape.*—Ovoid.
*Anther length.*—1 mm.
*Anther color.*—144D.
*Pollen amount.*—Scarce pollen.
*Pollen color.*—145D.

Gynoecium:
*Pistils quantity.*—1.
*Pistil length.*—18–22 mm.
*Stigma shape.*—Bi-lobed.
*Stigma color.*—144C.
*Style length.*—14–18 mm.
*Style color.*—144D.
*Ovary color.*—144C.

No seed set is observed.

Physiological and ecological characteristics: Good tolerance to heat and cold, from 2 to 36 degrees Celsius. No resistance to diseases common in *Verbena* is observed.

What is claimed is:

1. A new and distinct variety of *Verbena* plant named 'SCY', substantially as herein illustrated and described.

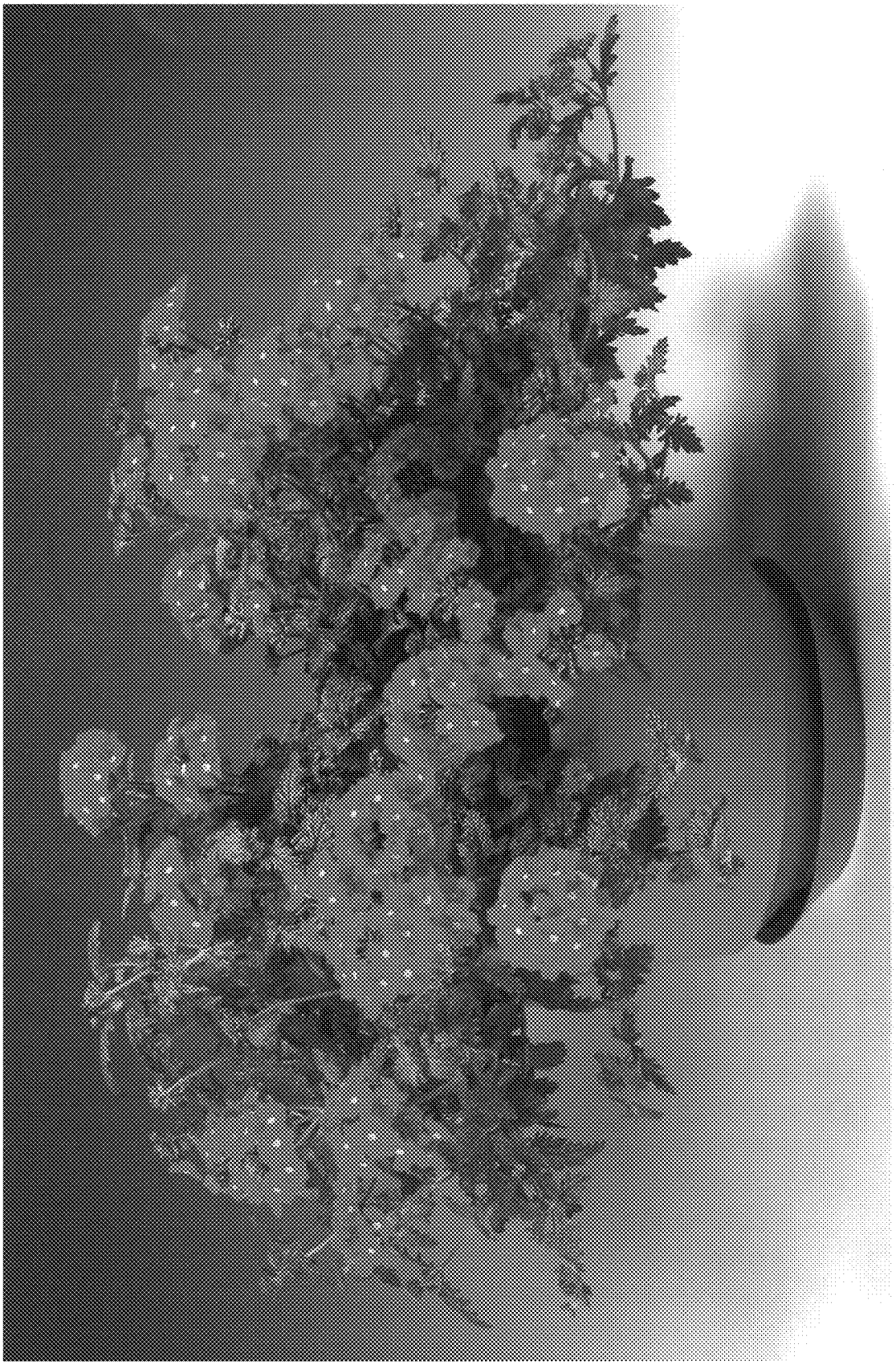

* * * * *